(12) United States Patent
Schneider et al.

(10) Patent No.: US 9,393,386 B2
(45) Date of Patent: Jul. 19, 2016

(54) INTRAVASCULAR DEVICE

(71) Applicant: Cagent Vascular, LLC, Wayne, PA (US)

(72) Inventors: Peter Schneider, Honolulu, HI (US); Robert M. Giasolli, Orange, CA (US)

(73) Assignee: Cagent Vascular, LLC, Wayne, PA (US)

( * ) Notice: Subject to any disclaimer, the term of this patent is extended or adjusted under 35 U.S.C. 154(b) by 227 days.

(21) Appl. No.: 13/689,657

(22) Filed: Nov. 29, 2012

(65) Prior Publication Data

US 2013/0165958 A1   Jun. 27, 2013

Related U.S. Application Data

(63) Continuation of application No. 12/408,035, filed on Mar. 20, 2009, now Pat. No. 8,323,243.

(60) Provisional application No. 61/038,477, filed on Mar. 21, 2008.

(51) Int. Cl.
  *A61M 25/10*      (2013.01)
  *A61B 17/22*      (2006.01)
  (Continued)

(52) U.S. Cl.
  CPC ............... *A61M 25/104* (2013.01); *A61B 17/22* (2013.01); *A61M 25/0082* (2013.01); *A61B 17/205* (2013.01); *A61B 17/320725* (2013.01); *A61B 2017/22061* (2013.01);
  (Continued)

(58) Field of Classification Search
  CPC ............... A61M 2025/105; A61M 2025/1086; A61M 25/104; A61M 2025/0096; A61M 25/0082; A61M 2025/109; A61F 2/848; A61B 17/22; A61B 2017/22061; A61B 17/320725

See application file for complete search history.

(56) References Cited

U.S. PATENT DOCUMENTS 3,221,746 A   12/1965 Noble
3,635,223 A   1/1972 Klieman
(Continued)

FOREIGN PATENT DOCUMENTS

EP       1604704       12/2005
WO       WO 02/43796    6/2002
(Continued)

OTHER PUBLICATIONS

Supplemental Search Report for European Application No. 09722111.3, mailed Jun. 29, 2011.
(Continued)

*Primary Examiner* — Kami A Bosworth
*Assistant Examiner* — Hamza Darb
(74) *Attorney, Agent, or Firm* — Knobbe, Martens, Olson & Bear LLP

(57) ABSTRACT

An intravascular device can comprise a carrier and an expansion apparatus. The device can be used for intravascular treatment of atherosclerotic plaque. The carrier can be reversibly expandable and collapsible within a vessel and can have ribbon strips extending between opposite ends in a longitudinal direction of the carrier. The ribbon strips can each be formed with a plurality of elongated protrusions thereon. The expansion apparatus can be used to actuate the ribbon strips each with the plurality elongated protrusions to pierce a luminal surface of the plaque with lines or patterns of microperforations which act as serrations for forming cleavage lines or planes in the plaque.

20 Claims, 18 Drawing Sheets

(51) Int. Cl.
*A61M 25/00* (2006.01)
*A61B 17/20* (2006.01)
*A61B 17/3207* (2006.01)

(52) U.S. Cl.
CPC . *A61M 2025/0096* (2013.01); *A61M 2025/109* (2013.01); *A61M 2025/1086* (2013.01)

(56) References Cited

U.S. PATENT DOCUMENTS

| | | | |
|---|---|---|---|
| 4,465,072 A | 8/1984 | Taheri | |
| 5,009,659 A | 4/1991 | Hamlin et al. | |
| 5,042,707 A | 8/1991 | Taheri | |
| 5,192,291 A | 3/1993 | Pannek, Jr. | |
| 5,196,024 A | 3/1993 | Barath | |
| 5,320,634 A | 6/1994 | Vigil et al. | |
| 5,336,234 A | 8/1994 | Vigil et al. | |
| 5,411,478 A | 5/1995 | Stillabower | |
| 5,423,851 A | 6/1995 | Samuels | |
| 5,501,689 A | 3/1996 | Green et al. | |
| 5,569,272 A | 10/1996 | Reed et al. | |
| 5,616,149 A | 4/1997 | Barath | |
| 5,665,116 A | 9/1997 | Chaisson et al. | |
| 5,681,346 A | 10/1997 | Orth et al. | |
| 5,713,860 A | 2/1998 | Kaplan et al. | |
| 5,720,726 A | 2/1998 | Marcadis et al. | |
| 5,797,935 A | 8/1998 | Barath | |
| 5,797,951 A | 8/1998 | Mueller | |
| 5,800,526 A | 9/1998 | Anderson et al. | |
| 5,868,779 A | 2/1999 | Ruiz | |
| 5,957,949 A | 9/1999 | Leonhardt et al. | |
| 6,007,543 A | 12/1999 | Ellis et al. | |
| 6,036,725 A | 3/2000 | Avellanet | |
| 6,048,332 A | 4/2000 | Duffy et al. | |
| 6,053,943 A | 4/2000 | Edwin et al. | |
| 6,102,904 A | 8/2000 | Vigil et al. | |
| 6,126,685 A | 10/2000 | Lenker et al. | |
| 6,197,013 B1 | 3/2001 | Reed et al. | |
| 6,221,102 B1 | 4/2001 | Baker et al. | |
| 6,280,414 B1 | 8/2001 | Shah et al. | |
| 6,290,728 B1 | 9/2001 | Phelps et al. | |
| 6,371,962 B1 | 4/2002 | Ellis et al. | |
| 6,475,237 B2 | 11/2002 | Drasler et al. | |
| 6,562,062 B2 | 5/2003 | Jenusaitis et al. | |
| 6,638,246 B1 | 10/2003 | Naimark et al. | |
| 6,692,504 B2 | 2/2004 | Kurz et al. | |
| 6,719,775 B2 | 4/2004 | Slaker et al. | |
| 6,942,680 B2 | 9/2005 | Grayzel et al. | |
| 7,007,698 B2 | 3/2006 | Thornton | |
| 7,087,088 B2 | 8/2006 | Berg et al. | |
| 7,179,284 B2 | 2/2007 | Khosravi et al. | |
| 7,211,101 B2 | 5/2007 | Carley et | |
| 7,270,673 B2 | 9/2007 | Yee et al. | |
| 7,303,572 B2 | 12/2007 | Melsheimer et al. | |
| 7,413,558 B2 | 8/2008 | Kelley et al. | |
| 7,500,986 B2 | 3/2009 | Lye et al. | |
| 7,611,484 B2 | 11/2009 | Wellman et al. | |
| 7,691,119 B2 | 4/2010 | Farnan | |
| 7,931,663 B2 | 4/2011 | Farnan et al. | |
| 8,323,243 B2 | 12/2012 | Schneider et al. | |
| 2001/0016726 A1 * | 8/2001 | Dubrul et al. | 604/509 |
| 2002/0010489 A1 | 1/2002 | Grayzel et al. | |
| 2002/0077594 A1 * | 6/2002 | Chien et al. | 604/103.02 |
| 2003/0065303 A1 | 4/2003 | Wellman et al. | |
| 2003/0153870 A1 | 8/2003 | Meyer et al. | |
| 2003/0158595 A1 | 8/2003 | Randall et al. | |
| 2003/0163148 A1 | 8/2003 | Wang et al. | |
| 2004/0106904 A1 | 6/2004 | Gonnelli et al. | |
| 2004/0143287 A1 | 7/2004 | Konstantino et al. | |
| 2004/0158270 A1 | 8/2004 | Wyzgala et al. | |
| 2004/0186551 A1 | 9/2004 | Kao et al. | |
| 2004/0249445 A1 | 12/2004 | Rosenthal et al. | |
| 2005/0021070 A1 | 1/2005 | Feld et al. | |
| 2005/0203388 A1 | 9/2005 | Carr | |
| 2005/0251164 A1 | 11/2005 | Gifford, III et al. | |
| 2005/0288764 A1 | 12/2005 | Snow et al. | |
| 2006/0122684 A1 | 6/2006 | Lye et al. | |
| 2007/0021774 A1 | 1/2007 | Hogendijk | |
| 2007/0093744 A1 | 4/2007 | Elmaleh | |
| 2007/0191766 A1 | 8/2007 | McMorrow | |
| 2007/0191811 A1 | 8/2007 | Berglund | |
| 2007/0213761 A1 | 9/2007 | Murphy et al. | |
| 2008/0015500 A1 * | 1/2008 | Herweck et al. | 604/103.01 |
| 2009/0157159 A1 | 6/2009 | Schneider et al. | |
| 2009/0214615 A1 | 8/2009 | Zhao | |
| 2010/0042121 A1 | 2/2010 | Schneider et al. | |
| 2010/0274188 A1 | 10/2010 | Chang et al. | |
| 2013/0211381 A1 | 8/2013 | Feld | |
| 2013/0218181 A1 | 8/2013 | Feld et al. | |
| 2013/0253426 A1 | 9/2013 | Campbell et al. | |
| 2014/0066898 A1 | 3/2014 | Cully et al. | |
| 2014/0066960 A1 | 3/2014 | Feld et al. | |

FOREIGN PATENT DOCUMENTS

| | | |
|---|---|---|
| WO | WO 02/078511 | 10/2002 |
| WO | WO 2006/130194 | 12/2006 |
| WO | WO 2008/020980 | 2/2008 |

OTHER PUBLICATIONS

Supplemental European Search Report for European Application No. 10817896.3 dated Jun. 19, 2013.

* cited by examiner

Configuration 3: patch

Configuration 4: spiral/diagonal

Figure 10A
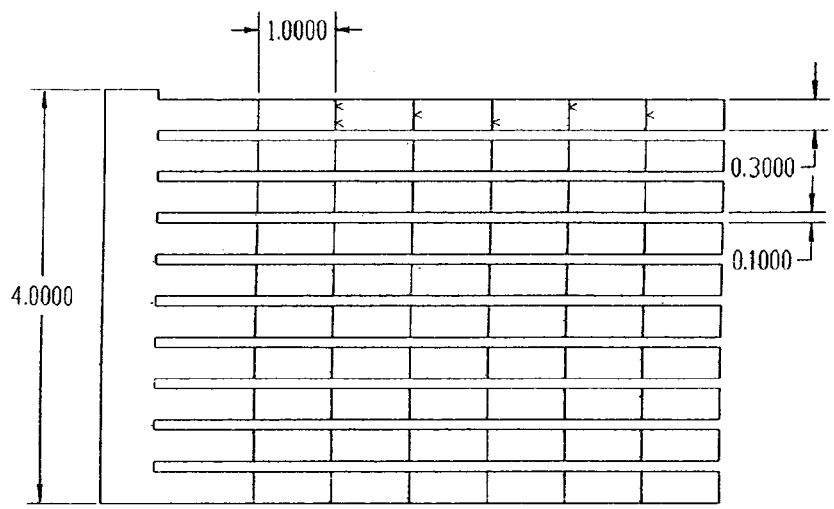
Figure 10B
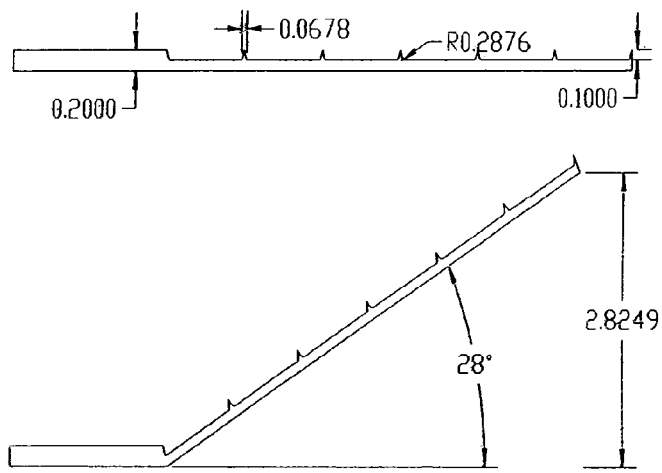
Figure 10C

Figure 11A
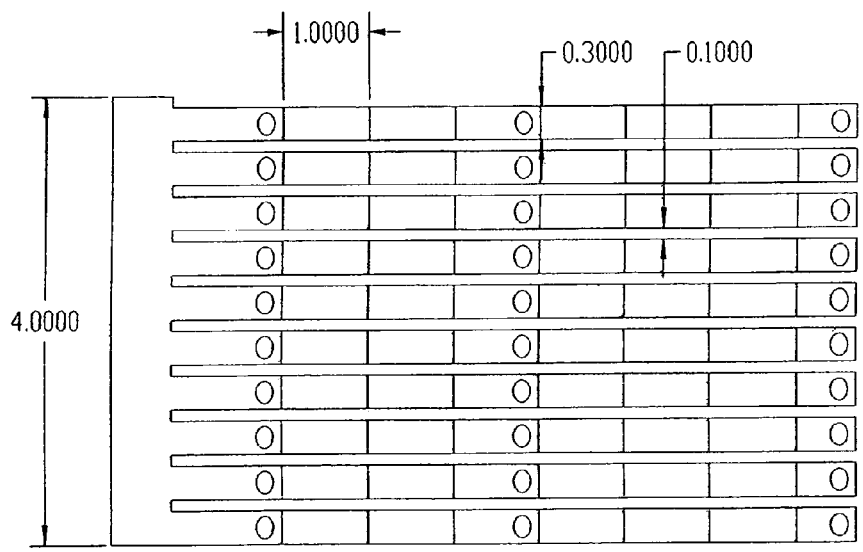
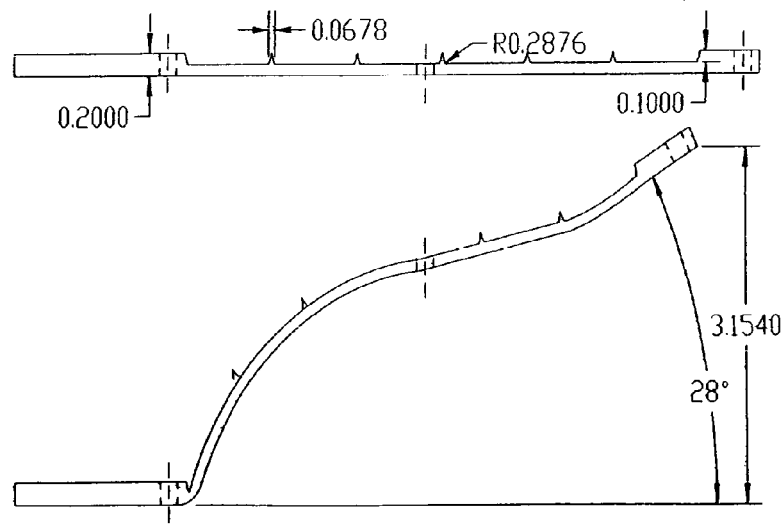
Figure 11B
Figure 11C

Figure 12A
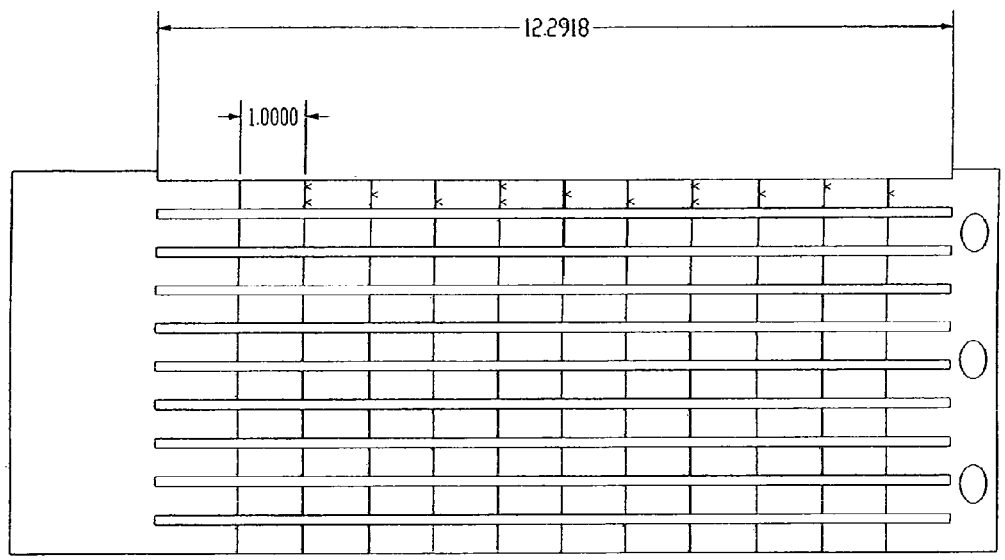
Figure 12B
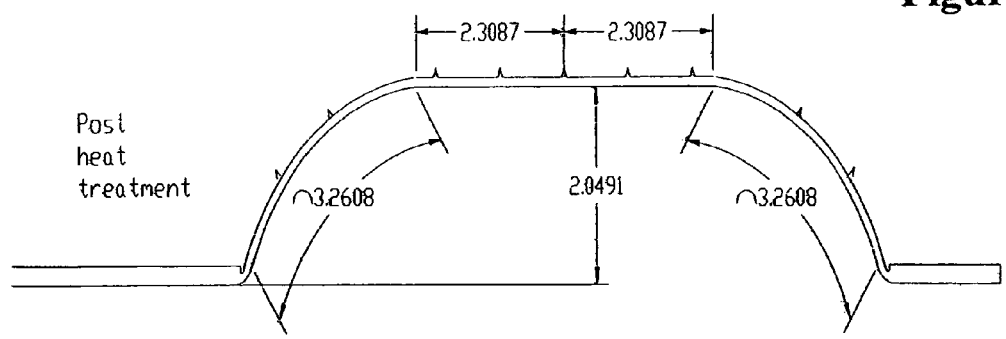
Figure 12C

INTRAVASCULAR DEVICE

CROSS-REFERENCE TO RELATED APPLICATIONS

This application is a continuation of U.S. application Ser. No. 12/408,035, filed Mar. 20, 2009, now U.S. Pat. No. 8,323, 243, which claims the benefit of priority to U.S. Provisional Application 61/038,477, filed Mar. 21, 2008. All of above applications are hereby incorporated by reference herein in their entirety and are to be considered part of this application.

FIELD OF THE INVENTION

The present invention is directed to a device and method for opening blood vessels in the body occluded by atherosclerotic plaque by pre-angioplasty serration and dilatation of the plaque.

BACKGROUND OF THE INVENTION

Atherosclerotic occlusive disease is the primary cause of stroke, heart attack, limb loss, and death in the US and the industrialized world. Atherosclerotic plaque farms a hard layer along the wall of an artery and is comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty.

Balloon angioplasty is an accepted and common method of opening blocked or narrowed blood vessels in every vascular bed in the body. Balloon angioplasty is performed with a balloon angioplasty catheter. The balloon angioplasty catheter consists of a cigar shaped, cylindrical balloon attached to a catheter. The balloon angioplasty catheter is placed into the artery from a remote access site that is created either percutaneously or through open exposure of the artery. The catheter 1 is passed along the inside of the blood vessel over a wire that guides the way of the catheter. The portion of the catheter with the balloon attached is placed at the location of the atherosclerotic plaque that requires treatment. The balloon is inflated to a size that is consistent with the original diameter of the artery prior to developing occlusive disease.

When the balloon is inflated, the plaque is stretched, compressed, fractured, or broken, depending on its composition, location, and the amount of pressure exerted by the balloon. The plaque is heterogeneous and may be soft in some areas or hard in others causing unpredictable cleavage planes to form under standard balloon angioplasty. The basic mechanism of balloon angioplasty relies to on a combination of actions caused by the balloon exerting pressure on the atherosclerotic plaque, including; compression of the plaque and the fracture of the hard, circumferentially calcified portion of the plaque. Balloon angioplasty causes plaque disruption and sometimes it causes arterial injury at the angioplasty site. Balloon angioplasty is often performed at high inflation pressures, in excess of 4 atmospheres, very commonly at 8 atm and sometimes up to 22 atm. Therefore, the results of balloon angioplasty are unpredictable.

When the angioplasty balloon is expanded with enough pressure to open a hard plaque dissection often occurs; the hardened areas become disrupted and partially separated from the arterial wall and are prone to lifting up as flaps or chunks. The higher the pressure of balloon angioplasty and the more rapidly the pressure reaches a high level, the more often it produces dissection. The random cleavage planes that are created by the dissection depend upon the composition of the plaque and the pressure exerted upon it. The cleavage planes tend to be wandering, longitudinal lines. The depth of the cleavage planes or fractures that are created by balloon angioplasty varies significantly and may be superficial or may be deep and extend all the way to the media of the arterial wall. To the extent that the cleavage plane goes across the line of flow, that is perpendicular or diagonal to the axial direction of the vessel, there is the potential for partial or complete lifting of a flap. When a flap of fractured plaque has lifted, it may cause acute occlusion or blockage of blood flow, or leave a significant residual stenosis, or may extend to create a larger flap.

Frequently, a segment of the plaque is more resistant to dilatation than the remainder of the plaque. When this occurs, greater pressure pumped into the balloon results in full dilatation of the balloon to its intended size. The balloon is deflated and removed and the artery segment is reexamined, usually using angiography. The process of balloon angioplasty is one of uncontrolled plaque disruption. The lumen of the blood vessel at the site of treatment is usually somewhat larger, but not always and not reliably. Some of the cleavage planes created by fracture of the plaque with balloon angioplasty form dissection. A dissection occurs when a portion of the plaque is lifted away from the artery and is not fully adherent and may be mobile or loose. The plaque that has been disrupted by dissection protrudes into the flowstream. If the plaque lifts completely in the direction of blood flow, it may impede flow or cause acute occlusion of the blood vessel.

The dissection of plaque after balloon angioplasty is treated to prevent occlusion and to resolve residual stenosis. A common practice has been to place a retaining structure, such as a rigid or semi-rigid tubular stent, to hold the artery open after angioplasty and retain the dissected plaque material back against the wall of the blood vessel to keep an adequate lumen open for blood flow. The clinical management of dissection or residual narrowing after balloon angioplasty is currently addressed through the development of increasingly complex stent structures. However, there has been substantial clinical evidence of disadvantages with using stents, including body rejection of a large mass of foreign material, and the emplacement of extensive surface area of a stent that may become sites for re-accumulation of plaque re-stenosis due to smooth muscle cell growth and intimal hyperplasia.

In juxtaposition to lesions that may develop significant dissection after balloon angioplasty, a substantial proportion of patients do not sustain major dissections as a result of balloon angioplasty. This seems to depend on several factors, including; the location and morphology of the lesion, and the pressure required to dilate the lesion during balloon angioplasty, but is also to some extent unpredictable. This situation does not require a stent. When post-angioplasty blood vessels show no sign or minimal sign of dissection and are left to heal on their own, i.e., when no stent is implanted, especially in the iliac and femoro-popliteal arteries, the rate of acute re-occlusion is low.

The long-term success of balloon angioplasty alone in many cases may produce the same or better long-term results than if a stent was emplaced. Balloon angioplasty without stenting therefore remains one of the most common endovascular procedures and one of the most cost effective.

When it is deemed necessary that a stent is required at a given site of plaque buildup, it is highly desirable to have the ability to fully dilate the stent within the lesion. This is a problem that has been the focus of intensive investigation and is due to the fact that some lesions are so recalcitrant to dilatation, that they cannot be dilated even at very high pressures.

Accordingly, it is deemed highly desirable to dilate plaque material so as to create a smooth post-angioplasty surface without elevated flaps or dissection, and to reduce the need for post-angioplasty stent placement. It is further desirable to provide a method of dilatation that permits better expansion of the lumen, such that if a stent is required, it allows the stent to be fully opened. In cases where local sites of post-angioplasty dissections or non-smooth lumen walls present themselves, it may be desirable to implant a retaining structure other than a stent which offers a minimal surface footprint and exerts low lateral pressures against the post-angioplasty surface.

SUMMARY OF THE INVENTION

To overcome the problems and disadvantages of prior practices of dilating plaque material in blood vessels through balloon angioplasty and with or without the use of post-angioplasty stent emplacement, the present invention employs an intravascular device carrying rows or patterns of small sharp spikes that are actuated by an expansion balloon or other apparatus to pierce the luminal surface of atherosclerotic plaque with lines or patterns of microperforations which act as serrations for forming cleavage lines, expansion lines, or planes in the plaque.

With the microperforation and serration procedure, the plaque can be compressed and the artery lumen safely and accurately dilated and stretched during balloon angioplasty to its intended diameter without creating numerous and substantial dissections and elevated flaps. The microperforation and serration enable the plaque to be dilated more evenly and smoothly and avoid forming random cracks that may lead to dissection and residual stenosis. The plaque, after it has been pre-treated with microperforation and serration, may also be dilated with lower pressure than that which is used in standard balloon angioplasty. The lower intra-balloon pressure (e.g., less than or equal to 4 atm and very often less than or equal to 2 atm) causes less disruption of the plaque, fewer dissections, and less injury to the artery wall. This "low pressure" or "minimal injury" angioplasty is less likely to cause the biological reaction that often follows balloon angioplasty with neointimal hyperplasia or smooth muscle cell replication.

In addition, microperforation and serration permits the plaque to expand with less fracturing or disruption of the plaque during balloon angioplasty. This decreases the need for stent placement to be used to treat dissection or residual stenosis after balloon angioplasty. If extensive dissections and non-smooth luminal wall surfaces require a stent to be placed, the improved dilatation of the lumen obtained with pre-angioplasty perforation and serration would allow a stent to be more fully opened.

In cases where one or more local sites of plaque dissections or flaps present themselves, a thin, ring-shaped tack device may be placed at only the location of each specific problem site, so that the amount of foreign material emplaced as a retaining structure in the blood vessel can be minimized and exert only low lateral pressures against the post-angioplasty surface. A novel method and device for applying a ring-shaped tack device as a retaining structure for plaque in the blood vessel is described in U.S. patent application Ser. No. 11/955,331, filed Dec. 12, 2007, entitled "Device for Tacking Plaque to Blood Vessel Wall", which is incorporated by reference herein.

Preferred embodiments of the perforation and serration device include three varying methods for spike deployment, through mechanical, balloon, and balloon-assist deployment. In a mechanical deployment method, lines or patterns of spikes protrude from a carrier surface or are extracted from the core of a catheter used for remote delivery. In a balloon deployment method, the spikes are mounted on an expandable balloon (similar to those used in angioplasty). In a balloon-assist method, the spikes are mounted on a carrier surface, and the carrier surface is pushed against the plaque under the expansion force of a balloon. The balloon in this method is used as means to stabilize the spikes within the artery and assist in pushing the spikes into the artery wall, but not to perform a simultaneous balloon angioplasty. Related methods are provided for insertion of the spikes in a compressed state into the blood vessel and expanding them to the intended shape for plaque microperforation and serration, and then re-seating the spikes for withdrawal. Several variations for spike mounting and delivery, and variations for spike cross-sectional profiles and for placement in lines and other patterns are further disclosed.

Preferred embodiments include a delivery device in which spikes are formed like polymer gum drops on a carrier ribbon or strip which are attached on the surface of an expansion balloon that is folded to a compact state for delivery. Another embodiment has spikes shaped as sharp pins carried on mesh bases and folded into flaps of an expansion balloon. Another embodiment of the delivery device has spikes that are deployed from and retracted back into a mechanical carrier. Another embodiment of the delivery device has spikes carried or projectable from the surface of a catheter carrier and an external multi-lobed balloon for pressing the spikes in circumferential sections against the plaque. Yet another embodiment has spikes carried on an accordion-like structure. The spikes may also be carried on ribbons strips of a slitted metal tube which are biased by shape memory outwardly toward the arterial wall. The spikes may be carried on a button structure for attachment to a carrier, or may be carried on a stretchable mesh structure over an expansion balloon. The spikes may be arranged in various patterns on the delivery device depending on the cleavage planes desired to be formed in the plaque.

In some embodiments an intravascular device can comprise a carrier and an expansion apparatus. The carrier can be reversibly expandable and collapsible within a vessel and can comprise a metal sheet formed in a tubular shape and can have ribbon strips extending between opposite ends of the sheet in a longitudinal direction of the carrier. The ribbon strips can each be formed with a plurality of elongated protrusions thereon, each of the protrusions attached to the ribbon strip at a base, a height of the protrusion defined by a distance extending from the base to a top edge, the top edge being elongate and extending essentially in a line that defines the top most portion of the protrusion. Each ribbon strip can be separated from adjacent ribbon strips by a single slit on either side which is oriented in the longitudinal direction and extends up to but not including one or both opposite ends of the tubular shape of metal sheet. The ribbon strips can be unconnected between said opposite ends of the tubular shape of metal sheet thereby being left free to expand into and form cleavage lines or planes in the plaque. The expansion apparatus can be used to actuate the ribbon strips each with the plurality elongated protrusions to pierce a luminal surface of the plaque with lines or patterns of microperforations which act as serrations for forming cleavage lines or planes in the plaque.

Other objects, features, and advantages of the present invention will be explained in the following detailed description of preferred embodiments with reference to the accompanying drawings.

BRIEF DESCRIPTION OF THE DRAWINGS

FIGS. 1A-1C illustrate a preferred embodiment of a delivery device in which FIG. 1A shows spikes formed like polymer gum drops on a carrier ribbon or strip, FIG. 1B shows attachment of the strips 16 on a balloon, and FIG. 1C shows a compact folded balloon.

FIGS. 2A-2F illustrate another preferred embodiment of the delivery device in which FIG. 2A shows the spike in the shape of a sharp pin, FIG. 2B shows how the pin is folded into a mesh, FIG. 2C shows the mesh annealed to the outer surface of an expansion balloon, FIG. 2D shows the pin folded into the mesh and under a flap of the balloon, FIG. 2e shows the pins deployed when the balloon is expanded, and FIG. 2F shows a detail view of the base of the pin.

FIGS. 10A-10C show another embodiment for the spike carrier of the delivery device in which the spikes are carried on ribbon strips of a slitted metal tube which are biased by shape memory outwardly toward the arterial wall.

FIGS. 11A-11C show a variation of the above-described embodiment in which the ribbons of the carrier sheet contain a series of holes.

FIGS. 12A-12C show another variation of the above-described embodiment in which the middle section of the carrier sheet has slitted ribbons which are biased outwardly toward the arterial wall.

DETAILED DESCRIPTION OF THE PREFERRED EMBODIMENT

Figure 1C:
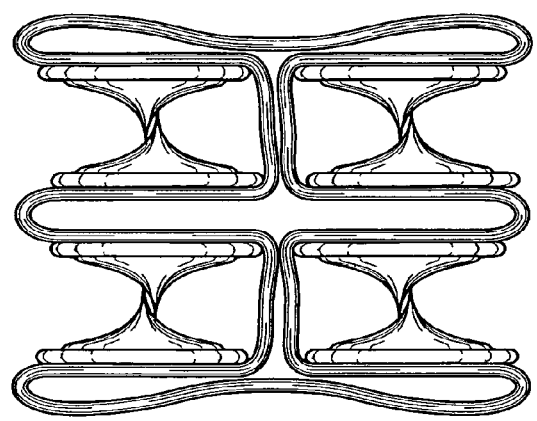

The conventional practice of compression of plaque by expansion pressure during balloon angioplasty, i.e., by applying a high pressure expansion force equally in all directions radially from the inside to a heterogeneous, roughly circumferential plaque-structure, can produce unpredictable and inconsistent results. In typical treatment of atherosclerotic plaques, the angioplasty balloon is inflated with 4 to 8 atmospheres of pressure, and pressures up to 22 atmospheres may be required in some cases. Such high pressures can cause injury to the intima and media in the artery at the treatment location. Arterial wall injury is one of the major stimulants to intimal hyperplasia, smooth muscle cell replication and intravascular scarring causing occlusion. Plaque is heterogeneous in nature composed of varying masses of soft and hard materials, calcium and highly variable topography, and can give way along paths of least resistance. Therefore, when standard balloon angioplasty is performed, some of the plaque inevitably fractures. The extent and severity of the fracture, the angiographic result and the morphology of the artery surface that result will vary significantly from one patient to the next. This leads to many cases in which stents are required to be implanted, which prolongs the surgical procedure, and increases medical risk and costs. Moreover, the clinical evidence indicates substantial disadvantages with using stents, including body rejection of a large mass of foreign material, and the emplacement of extensive surface area of a stent that may become sites for re-accumulation of plaque and re-stenosis. There is some evidence that stents may stimulate biological reaction that limits the long-term patency of the procedure. Stent also cause problems with kinking of the artery in areas where the artery is significantly flexed, such as at the knee joint. Stents may also fracture and break due to material stress.

In the present invention, the plaque is treated by a perforation and serration procedure that forms lines or patterns of microperforations which act as serrations for forming cleavage lines or planes in the plaque. The serrations will result in more predictable and more uniform expansion characteristics in the plaque during a subsequent balloon angioplasty, thereby helping to make the balloon angioplasty a more consistent and predictable process. It is expected that plaque prepared by the perforation and serration procedure can be dilated with a much lower pressure during angioplasty, i.e., less than 4 atmospheres, and as low as 2 atmospheres or less. The ability to perform angioplasty at lower pressures will create less plaque dissection and less arterial injury. Less arterial injury may lead to better rates of acute success because there is less dissection, and may also lead to better long-term results since there is less injury to the intima and media in the artery at the treatment location.

The forming of serrations in the plaque through microperforation is deemed to provide a line along which expansion energy may be released. The microperforations are formed in a pre-angioplasty procedure of inserting a carrier carrying an array of small, sharp spikes which are pressed under a slight expansion force to pierce partway into the plaque and without causing injury to the arterial walls. Since plaque usually fractures longitudinally during standard balloon angioplasty, the spikes are preferably arranged in a mostly longitudinal pattern. Other variations include configurations with a diagonal or zig-zag pattern consistent with the expected ways that plaque commonly fractures. The height of the spikes is designed to pierce the plaque surface to create serrations for expansion lines, but not deep enough to cut though the plaque thickness. Materials research on crack propagation can be applied to select the optimal configurations for spike patterning to obtain the best characteristics in plaque compression.

Artery vessels are comprised of organized lamellar structure with repeating structural and functional units of elastin, collagen and smooth muscle cells. The lamellar structure is prone to split and create a cleavage between adjacent elastic lamellae. Basically, in angioplasty the expansion is partly due to the arterial stretching. In addition the plaque material has low ductility and fracture stresses can propagate non-uniform cracks in the brittle material. In the pre-angioplasty preparation of the plaque material, the microperforations act as nucleation sites for void formation. In the subsequent application of balloon angioplasty, stress energy for compressing the plaque is released along the serration created by the series of pinpoint voids formed in the plaque to control crack propagation. If balloon angioplasty is applied without the plaque serration step, the amount of stress energy applied can be very high prior to initiation of crack formation, and once the crack begins the energy can quickly propagate along brittle crack areas, leading to unpredictable plaque ripping, tearing, or dissecting. The pre-angioplasty preparation of the plaque with microperforations avoids high stress concentration at an initial point of fracture, and assists stress release along the series of voids designed to guide the fissure event and provide more predictable cleavage lines in the plaque.

The perforation and serration procedure will promote more uniform compression of the plaque under expansion pressure during angioplasty. The portion of the plaque that does not compress will expand better and will be less likely to break or fracture. Forming serrations in the surface of the plaque is expected to provide better and more uniform compression under low pressures in angioplasty and will produce better plaque compression characteristics than the standard approach of applying high expansion pressures against the full length, width, and thickness of the plaque. This is expected to result in compressing the plaque with fewer tendencies for dissection, allowing the plaque to open along more natural lines, and therefore expanding the lumen larger and without causing arterial injury.

The perforation and serration procedure is expected to provide significant advantages as compared to prior proposals for cutting or scoring the plaque with blades or sharp edges. Some prior proposals have called for performing balloon angioplasty with longitudinal cutting blades affixed to the sides of the angioplasty balloon. However, when the balloon is expanded, the cutting blades are forced into the walls of the artery. Moreover, at the typical high pressures for balloon angioplasty, the cutting blades may be forced into the arterial walls at high pressure, because all the force of the balloon is concentrated on the projecting cutting blades. Because the cutting action of the blade is performed at the same time as the expansion of the artery with balloon angioplasty, there is no a prior preparation of the plaque before balloon angioplasty and there is a risk that the artery itself may be cut and forced open and will expand as it is forced. The artery may thus be injured in a traumatic manner and at high pressures. Cutting blades or edges also have relatively long linear lengths that will cut across non-uniform plaque material, producing uneven cuts. Even smaller cutting blades will encounter at times areas of dense calcification among softer masses that could be fractured by the linear cutting blades or edges. In contrast, microperforations form tiny holes at specific prick points across the plaque mass and taken together as a line or pattern of perforations result in more reliable serrations.

Other prior proposals have suggested scoring the plaque with a metal wire or tabs arranged around an angioplasty balloon in a spiral or double spiral manner. The outer wire or tabs may be forced into the wall of the artery when the balloon is expanded during angioplasty at high pressure. The orientation of the wire on the outside of the angioplasty balloon focuses the expanding balloon pressure on the wire. Therefore the pressure exerted by the wire against the wall of the artery far exceeds the pressure in the balloon generating a very high localized pressure at the working tip of the wire. The wire or tabs may cut deeply into the wall and may cause increased injury beyond that caused by the high pressure alone. In addition, because the wire is wrapped around the balloon in a spiral manner, the distance between the wire windings around the outside of the balloon will change at different balloon diameters. This causes some axial displacement of the wires so that it may actually undermine artery plaque by causing it to "dig up" the plaque. This may even create dissection planes that are more circumferentially oriented (as opposed to longitudinal) and may be more likely to function as flow limiting dissections.

In contrast, the perforation and serration procedure can be performed at low balloon or other expansion pressures. The microperforations are formed by small sharp spikes which can pierce into the plaque without digging it up. Forming tiny prick points with the small spikes will leave most of the surface of the plaque intact, will not injure the arterial wall, and will leave most of the plaque structure intact for more predictable and better compression characteristics. The serrations allow the plaque to be compressed at lower pressures during the following angioplasty. The plaque is also less likely to form dissections, both because it can be treated at lower pressures, and because the plaque has expansion lines serrated in it that allow it to expand in a more orderly manner.

Because the perforation and serration procedure forms small prick points in the plaque, it may also afford a very effective means of distributing anti-plaque medication into the plaque from a drug-eluting balloon during angioplasty or from a drug-eluting stent after angioplasty. The microperforations may serve to retain more medication within the plaque mass, acting as a portal to the inner structure of the plaque for the medication to work. In the pre-angioplasty procedure, the spikes may also be used as a carrier for drug delivery by-coating the spikes themselves with drugs.

The perforation and serration procedure is thus designed as a minimally invasive approach for creating predictable cleavage planes in atherosclerotic plaque in preparation for balloon angioplasty. The cleavage planes are enabled by the serrations formed by numerous small perforations into the plaque in a predetermined pattern on the plaque surface. By creating a preformed expansion line or line of cleavage prior to angioplasty, the artery is prepared so that it will respond to balloon dilatation in a more predictable manner with less likelihood of dissection or elevated surface flaps. The need for stent placement to smooth the artery surface and retain plaque dissections or flaps can thus be significantly decreased.

A suitable device for performing the perforation and serration procedure may be designed in a number of ways, as described below for the following preferred embodiments which are illustrative of the principles of the present invention. Three different methods for spike deployment, through mechanical, balloon, and balloon-assist deployment, are described with respect to certain preferred delivery designs. The locations, length, and configuration of the spikes may be designed for varying types of lesions and arterial sites being treated. For example, heavily calcified lesions may require that the spikes be more closely spaced and penetrate a little deeper into the plaque. Some device designs may only be partially covered with spikes so that the hardest part of the plaque is left alone and serrations are created along a softer portion of the plaque surface. Lesions that are more longitudinally oriented may require spike placements that are farther apart and arranged in a gradual twirling configuration.

Figure 1:
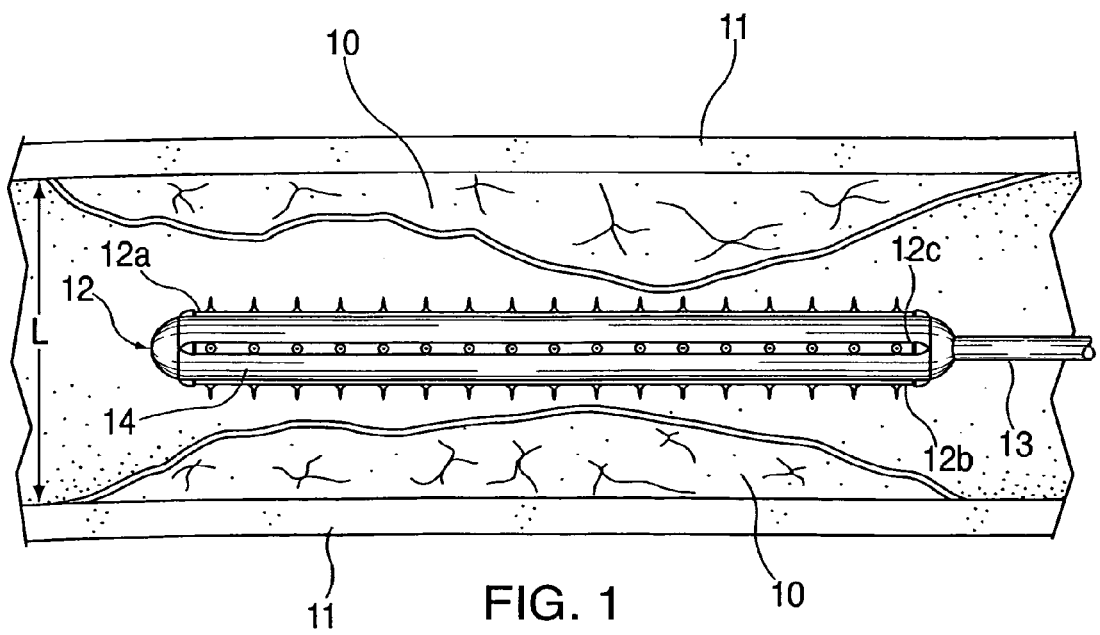
FIG. 1 shows a schematic illustration of the invention method for perforation and serration treatment of atherosclerotic plaque.

FIG. 1 shows a schematic illustration of the invention method for perforation and serration treatment of plaque 10 at a site in an artery 11 with a delivery device 12 for serration and dilatation of the plaque. The lumen L is the flow opening in the artery that has been occluded by plaque 10. The device 12 has one or more arrays 12a, 12b, and 12c of small, sharp spikes carried on carrier strips of surfaces which are seated on the outer surface of an expansion balloon 14 or other expansion device. The spikes are mounted on the carrier strips at spaced intervals and extend typically a distance 0.05 mm to 1.0 mm beyond the carrier surface for piercing into the plaque and forming microperforations across the surface of the plaque. The delivery device 12 may be carried in a catheter and positioned at the plaque site by insertion into the artery through a surgical incision (not shown) and manipulated into position by a wire 13 to the location of the plaque. The spikes and expansion balloon are initially in a deflated or collapsed state to allow threading of the device 12 through the artery.

When the delivery device is in position, and a catheter shield (if used) is retracted, the expansion balloon is inflated through an inlet tube 13 at low gas or fluid pressures to gently push the spike arrays against the plaque 10. Gas or fluid pressures in the range of 1 to 4 atm may be used for the pre-angioplasty procedure. The spikes create series of microperforations which act as serrations along the horizontal length of the plaque. The serrations allow cleavage lines or planes to be formed in the plaque at these locations under compression forces during a following angioplasty procedure. As the spikes are pressed into the plaque, the plaque is also compressed gently for a given measure of dilatation. When the serration has been performed, the balloon is deflated by suction of fluid or gas out through the tube, such that the delivery device 12 can resume its collapsed state so that it can be withdrawn from the artery.

A standard angioplasty balloon may thereafter be used to compress the plaque against the artery walls to open the lumen. The compression of the plaque during angioplasty can take place evenly and with minimal dissection or cracking along the cleavage lines formed by the microperforations. Due to the pre-angioplasty preparation of the plaque, the balloon angioplasty can be performed at low pressures of less than 4 atmospheres, and as low as 2 atmospheres of pressure or less. If the pre-angioplasty procedure has compressed the plaque sufficiently, it may not be necessary to follow it with a standard angioplasty.

Figure 1A:
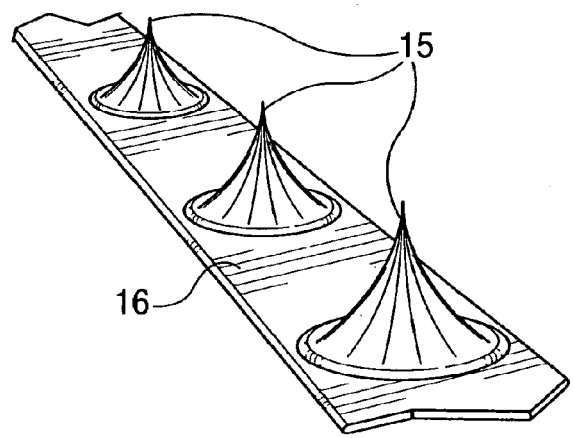

FIG. 1A illustrates a preferred embodiment of the delivery device in which the spikes are formed like polymer gum drops 15 on a narrow ribbon 16. The polymer is heated and fed in liquid form to an ejector that ejects a drop in position on the ribbon. The drop rapidly cools as it is ejected, and forms an inverted cone shape that comes to a hard sharp point by tapering off the fluid from the ejector. The potential shape of the spike can include other types of pointed shapes, such as a long, pyramidal shape, a tri angle shape, an arrow shape (longer and sharp in one axis and narrow and dull in the perpendicular axis), a gum drop shape, a narrow rectangle shape, a pin shape, a needle shape, and others. Other materials could be used to form the spike, including a pliable metal, such as Nitinol, or carbon nanotubes.

Figure 1B:
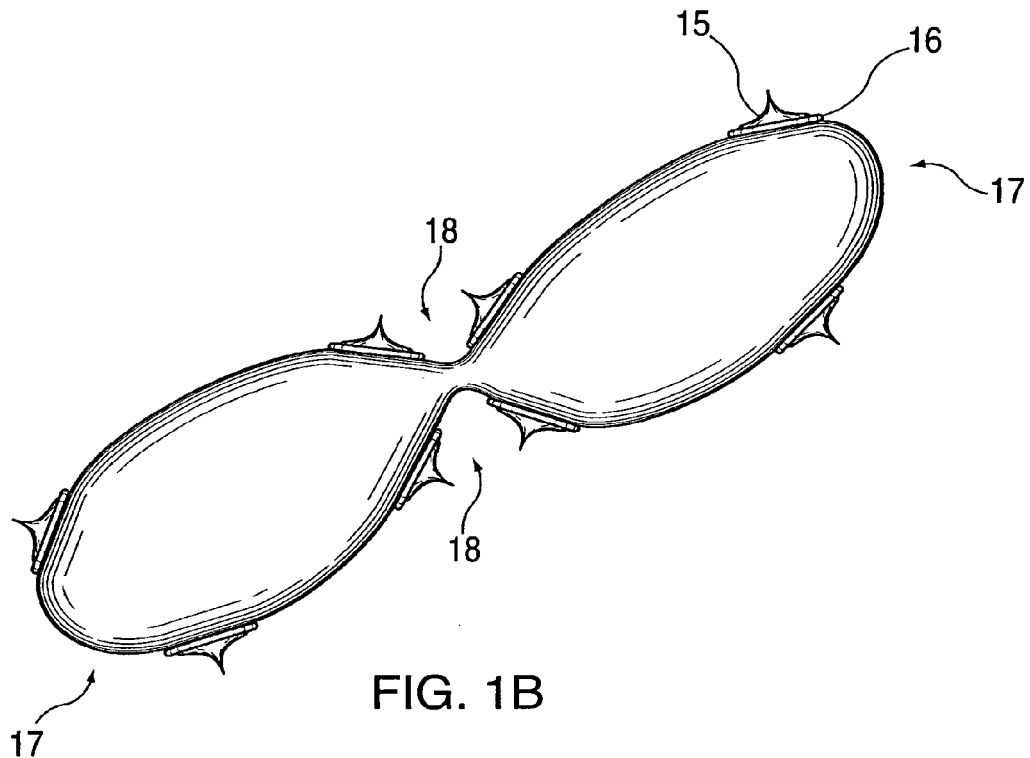

After hardening and processing of the polymer, the narrow strip 16 is annealed to the surface of an expansion balloon or other mechanically expansive carrier. The strips may also be interwoven into a mesh (polymer, metallic, or fabric). The strips or mesh are arranged in a pattern that envelopes the surface of the expansion balloon or other mechanically expansive structure. FIG. 1B shows attachment of the strips 16 (end view) along the longitudinal length of a balloon 17 at a number (8) of circumferential positions. The balloon may be folded at folds 18 to bring the sharp points 15 on four adjacent strips to nest with those of the other strip, and then the two lobes of the balloon are folded over again to bring the sharp points of the other four adjacent strips into nested configuration. FIG. 1C illustrates the resulting, compact folded balloon in which all the sharp points are folded within to avoid engaging the plaque material when the device is being moved into position.

Figure 2A:
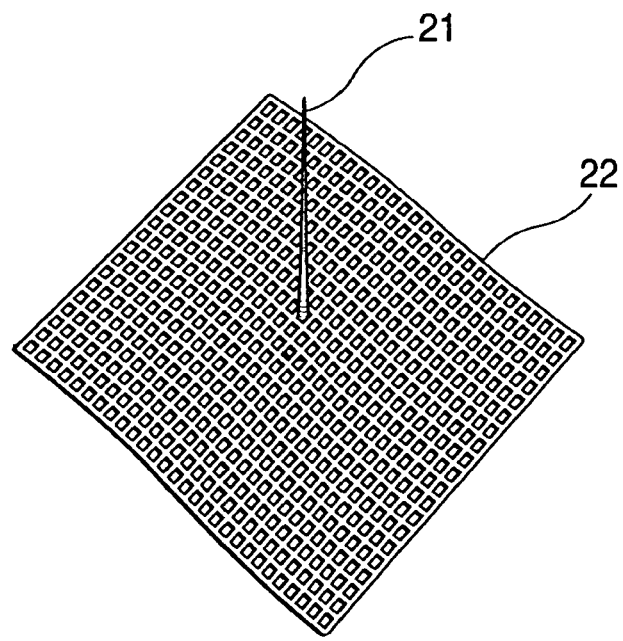

FIG. 2A illustrates another preferred embodiment in which the spike is in the shape of a sharp pin 21 that has a lower end bonded to a mesh 22 that is annealed to the surface of the expansion balloon. The lower end of the pin 21 is held by the polymer mesh so that the spike stands erect on the surface of the balloon when the balloon is inflated. The pin 21 may be constructed of polymer, metal composite, silicon or carbon composite or carbon nanotubes (single or multi wall).

Figure 2B:
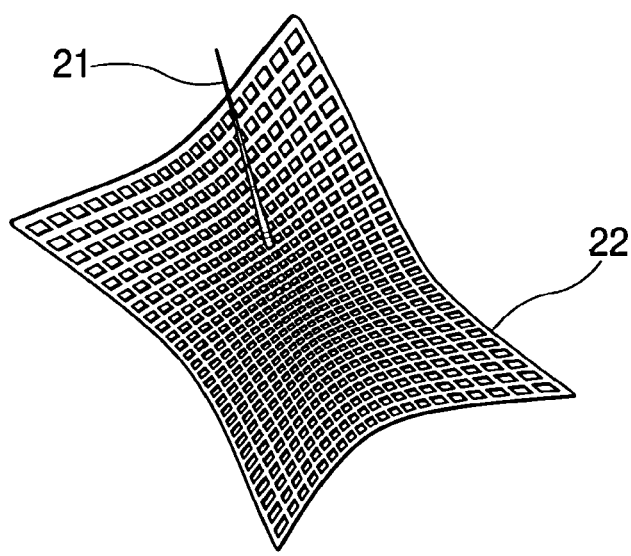
Figure 2C:
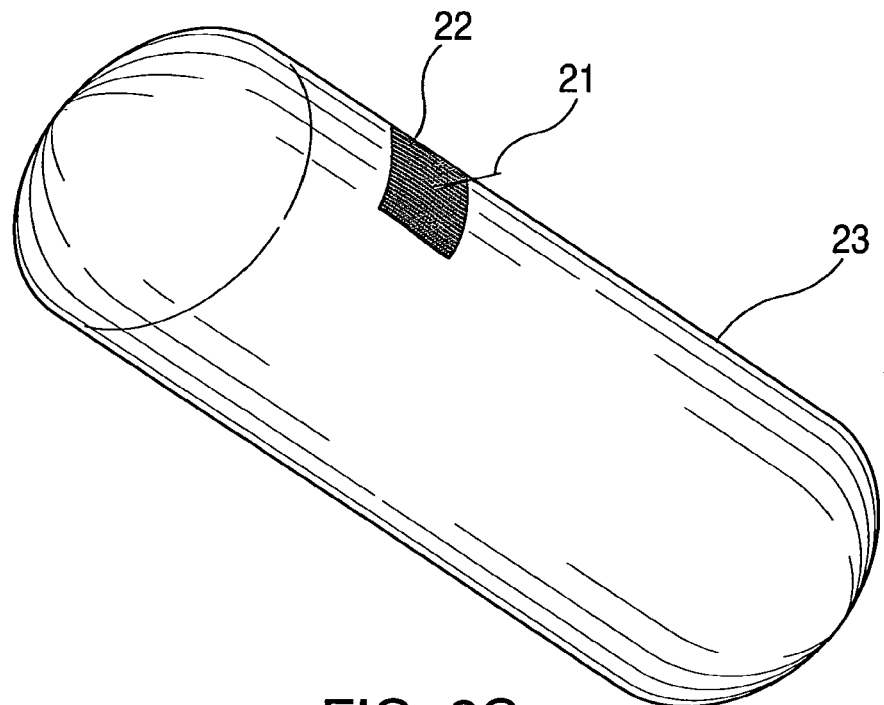
Figure 2D:
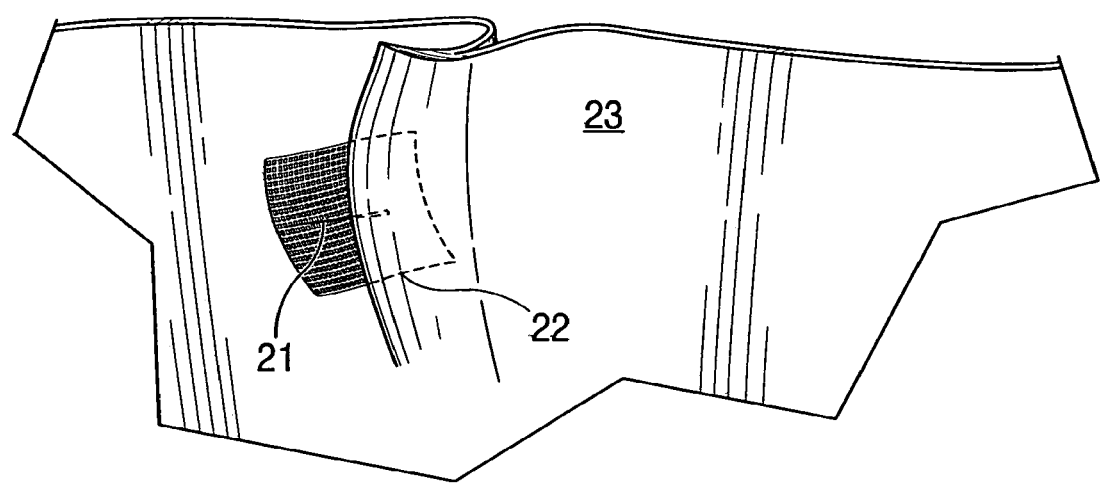

FIG. 2B illustrates how the pin 21 is folded by pressing it into the mesh 22. In FIG. 2C, the mesh 22 is shown annealed to the outer surface of the expansion balloon 23. In FIG. 2D, the pin 21 is laid down laterally and perpendicularly to the axis of the balloon-center line for placement, so that the pin is folded into the mesh and under a flap of the balloon. The entire mesh in the depressed mode is nearly swallowed up by the balloon material. With the pin laid down flat within the mesh, the balloon is protected from puncture of the balloon surface. The flap on the balloon unfolds during balloon expansion, and the meshes are unfolded so that the pins are quickly popped out straight and erect.

Figure 2E:
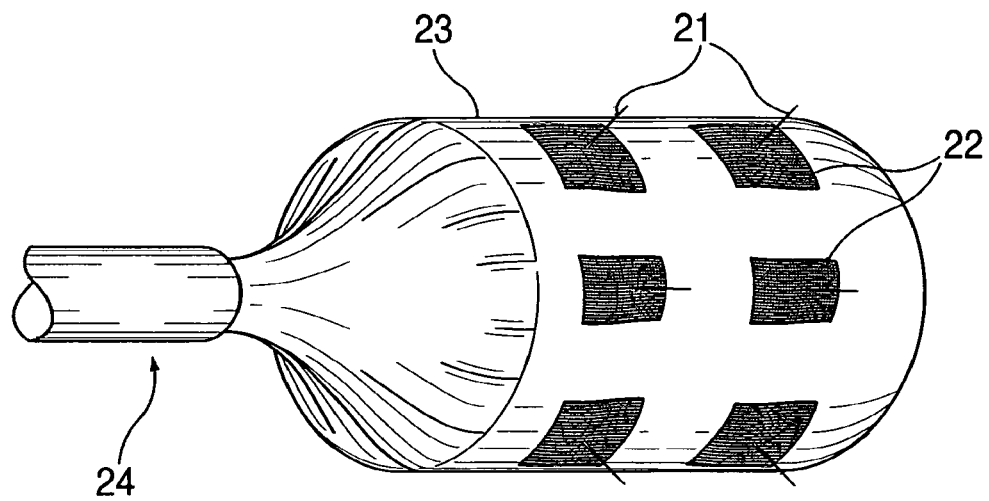
Figure 2F:
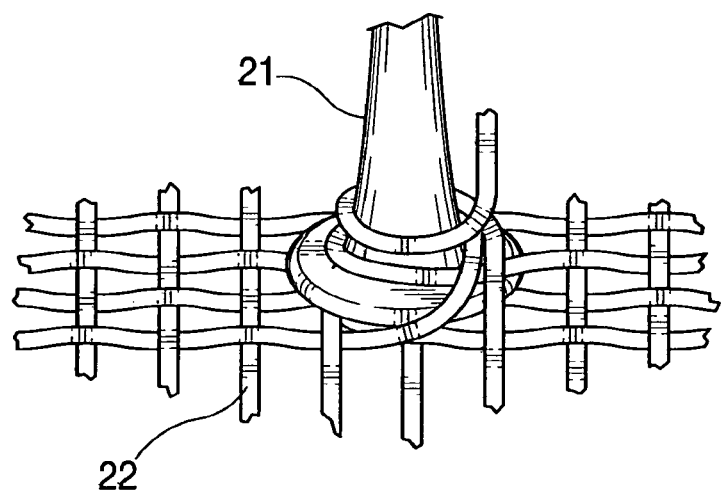

FIG. 2E shows the pins 21 deployed and standing erect on the expansion balloon 23 after the catheter shield 24 is withdrawn and the balloon is inflated. The pins are exposed and stand erect on the mesh sheets 22 that are mounted on the balloon surface. The pins stick out peripherally and can pierce into the plaque as the balloon is further inflated. FIG. 2F shows a detail of the base of the pin 21 entwined in the mesh weaving to center the lower end of the pin on the mesh 22 and hold the pin erect when the mesh is unfolded and the balloon is expanded.

Figure 3:
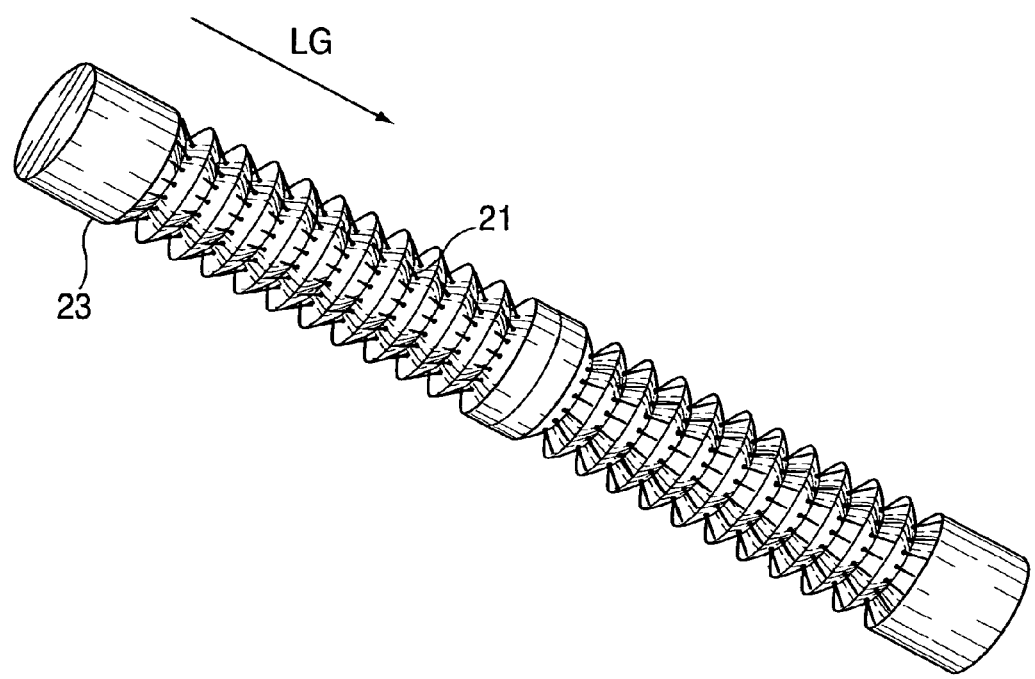
FIG. 3 shows the arrays of pins in the above-described embodiment folded within accordion-like flaps along the length of the expansion balloon.

In FIG. 3, arrays of pins 21 are shown folded within accordion-like flaps of a pre-angioplasty expansion balloon 23 of the device which are folded in alignment with a longitudinal axis LG of the balloon. In this design, half the flaps and pins are folded toward one end of the balloon, and the other half are folded toward the other end of the balloon. When the balloon is expanded, the mesh strips will reorient with respect to the surface of the balloon and face outward toward the plaque on the artery walls. The flaps of balloon material between parallel rows of spikes can be made extra flexible and pliable and may be formed as a folding crease. When gas or fluid pressure is injected in the balloon, the flaps are the first areas to pop out and help to point the spikes outwardly toward the plaque.

Figure 4A:
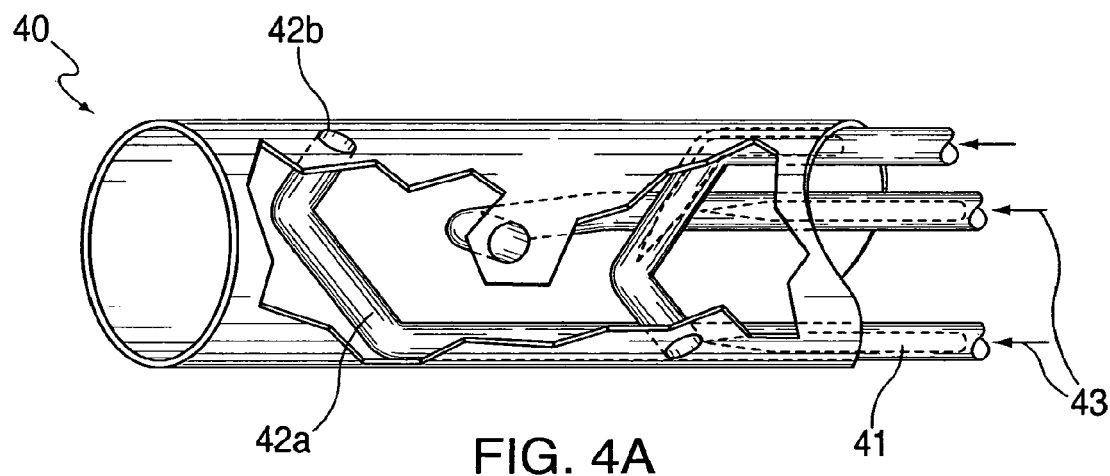
FIGS. 4A and 4B illustrate another embodiment of the delivery device in which spikes are deployed from and retracted back into a mechanical carrier.
Figure 4B:
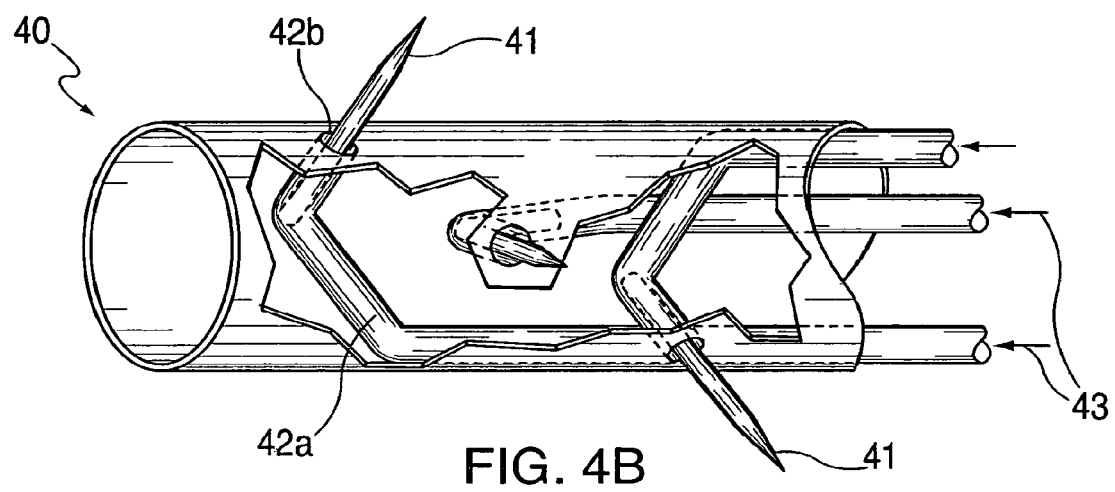

FIGS. 4A and 4B illustrate another embodiment of the delivery device in which an expansion balloon is not used but rather the spikes 41 are deployed from and retracted back into a mechanical carrier 40. The carrier has a plurality of tunnels 42a in its interior each of which holds a spike in a ready position within and has a spike exit hole 42b with its axis oriented radially to the outer surface of the carrier. When the carrier 40 is in position at a plaque site, the spikes are mechanically or hydraulically actuated, such as by a gas or fluid pressure force indicated by arrows 43, to travel through the tunnels and project radially from the spike exit holes 42b. The spikes have sharp points at their tips for creating microperforations in the plaque, but are flexible in their shafts so that they can be deployed from a laying down position and turned to a 90 degree standing up position. In that position, the spikes are pointed toward the wall of the artery and the plaque. As an alternative for mechanical actuation, the spikes may be actuated by respective levers which are pulled or pushed by a cable. Other types of mechanisms similarly may be used for mechanically deploying the spikes from the carrier.

FIGS. 5A-5D illustrate other embodiments of the delivery device for pre-angioplasty serration and dilatation. In the embodiment shown in FIG. 5A, rows of spikes 51 are bonded to a ribbon, rod, tri angle or other shaped carrier 50. An outer balloon 52 is divided into quadrants and shaped with cutout areas that conform to spaces in between the spikes. The balloon 52 is inflatable in quadrants circumferentially around the carrier 50. As one quadrant of the balloon 52 is inflated, the spikes on the opposing side of the carrier 50 are pressed into the plaque on the artery wall. The balloon 52 on the side of the one quadrant is deflated, then the next quadrant is inflated to press the spikes on another opposing side into a next section of the plaque. This is repeated for the other quadrants as needed until the spikes on all sides have been pricked into the circumference of the plaque surface.

Figure 5A:
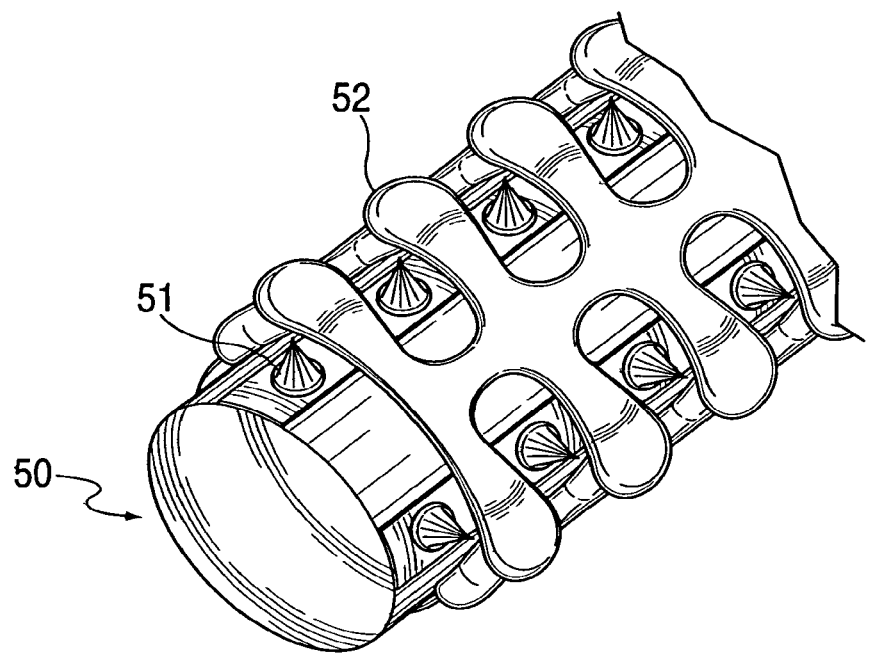
FIGS. 5A-5D illustrate other embodiments of the delivery device which has spikes carried or projectable from the surface of a catheter carrier and an external multi-lobed balloon for pressing the spikes in circumferential sections against the plaque.
Figure 5B:
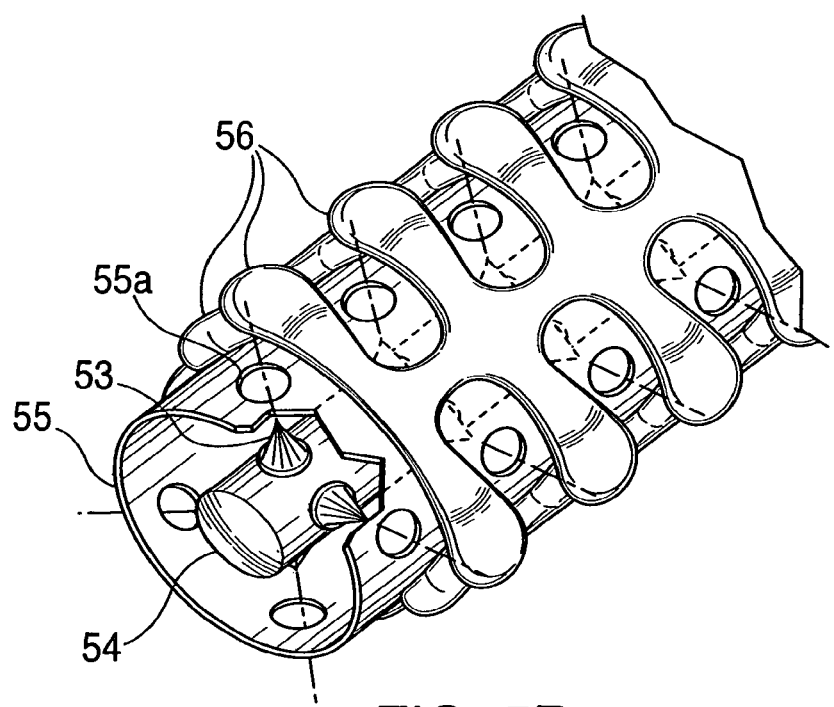

In FIG. 5B, another embodiment of the delivery device has rows or ribbons of spikes 53 bonded to an internal carrier balloon 54 sleeved inside of a tube 55 which has spike holes 55a aligned with the positions of the spikes spacing found on the internal carrier balloon 54. An outer balloon 56 is shaped with cutout areas that conform to the spaces between the spike holes. The outer balloon is able to be filled in quadrants circumferentially around the carrier device. As one quadrant expands, the tube is pressed on its opposing side against the plaque. The internal carrier balloon 54 is inflated and the spikes are pressed out of the holes and pierce into the plaque on the side in contact with the plaque. This is repeated for the remaining quadrants until the spikes have been pricked into the circumference of the plaque surface.

In the above-described embodiments, the multi-lobed segments of the expanding balloon stabilize and support the spikes as they enter the plaque to cause perforation. The spikes may be constructed of any suitable material, such as polymer, pliable metal, or carbon nanotubes, and may have one of many possible shapes, including a pin shape, a needle shape, a long, pyramidal shape, a triangle shape, an arrow shape, a gum drop shape, a narrow rectangle shape, and others. The balloon, as it is expanded, is also used to compress the plaque to a certain degree and dilate the lumen of the artery. The balloon may be manufactured to be inflated with $CO_2$ or with liquid.

Figure 5C:
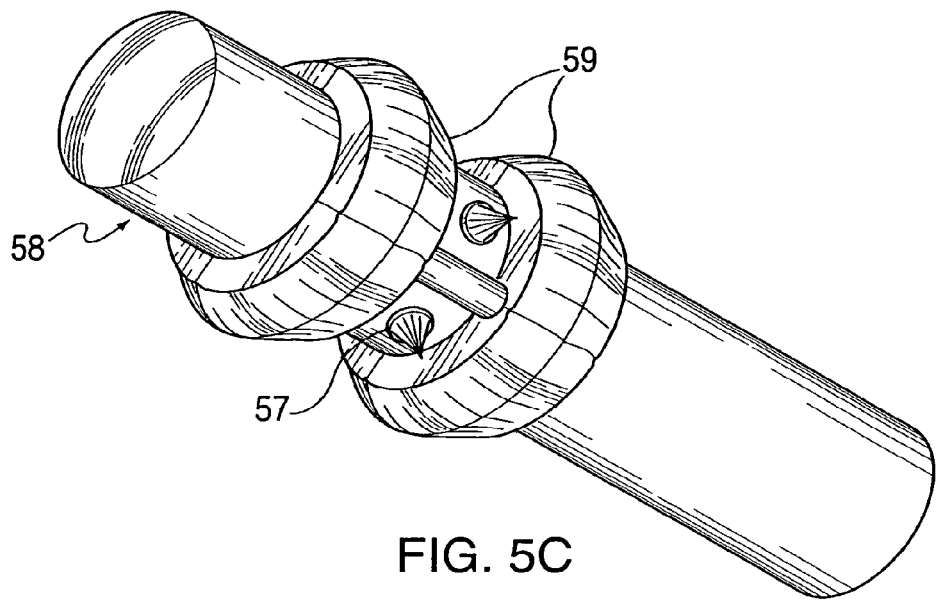
Figure 5D:
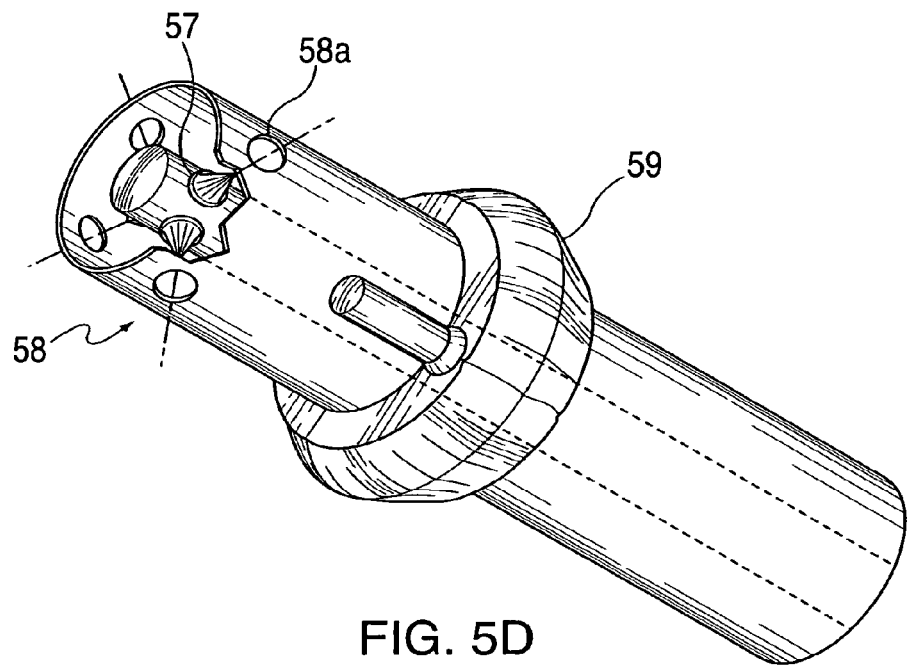

FIG. 5C shows another embodiment where rows of spikes 57 are bonded to or etched out of a ribbon, rod, triangle or other shaped carrier 58. An outer balloon 59 is multi-lobed capable of being inflated in sections and conforming to spaces in between the spikes. FIG. 5D shows a further embodiment in which the spikes 57 are seated on an inner balloon in a delivery catheter 58. The catheter walls have holes 58a located to allow the spikes to poke through when the inner balloon is inflated. On the outside of the catheter in this embodiment is multi-lobed external balloon 59 which is inflatable in sections. As one section is inflated, the catheter wall on the opposite side is pushed against the plaque on the arterial wall, and when the inner balloon is inflated, the spikes 57 are pressed out to pierce into the plaque mass. This procedure is repeated in sections circumferentially around the catheter until all areas of the plaque have been pierced by the spikes.

Figure 6A:
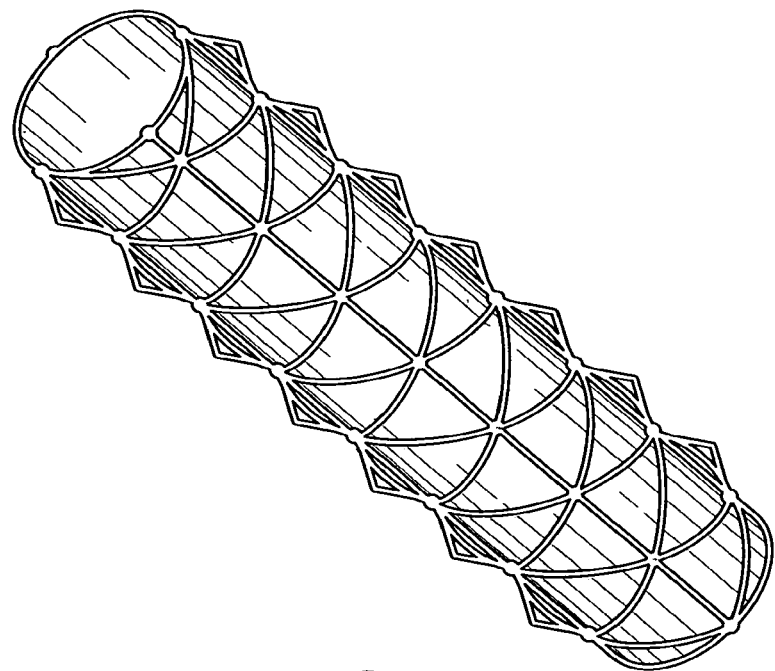
FIGS. 6A-6C show another embodiment for the delivery device in which the spikes are carried on an accordion-like structure
Figure 6B:
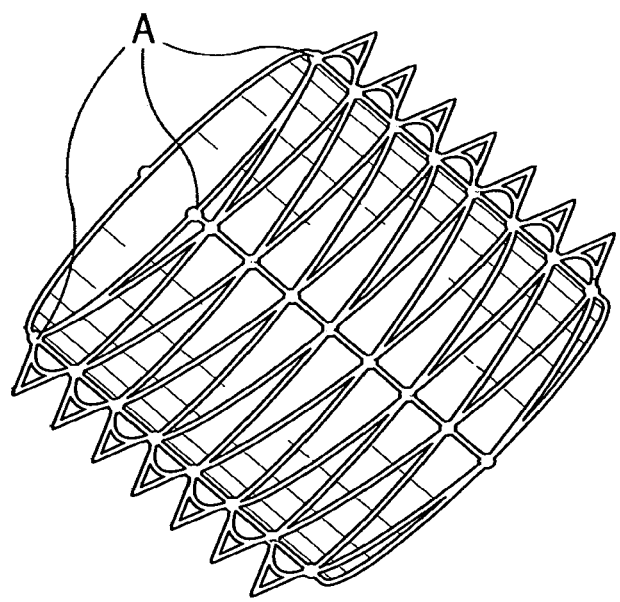
Figure 6C:
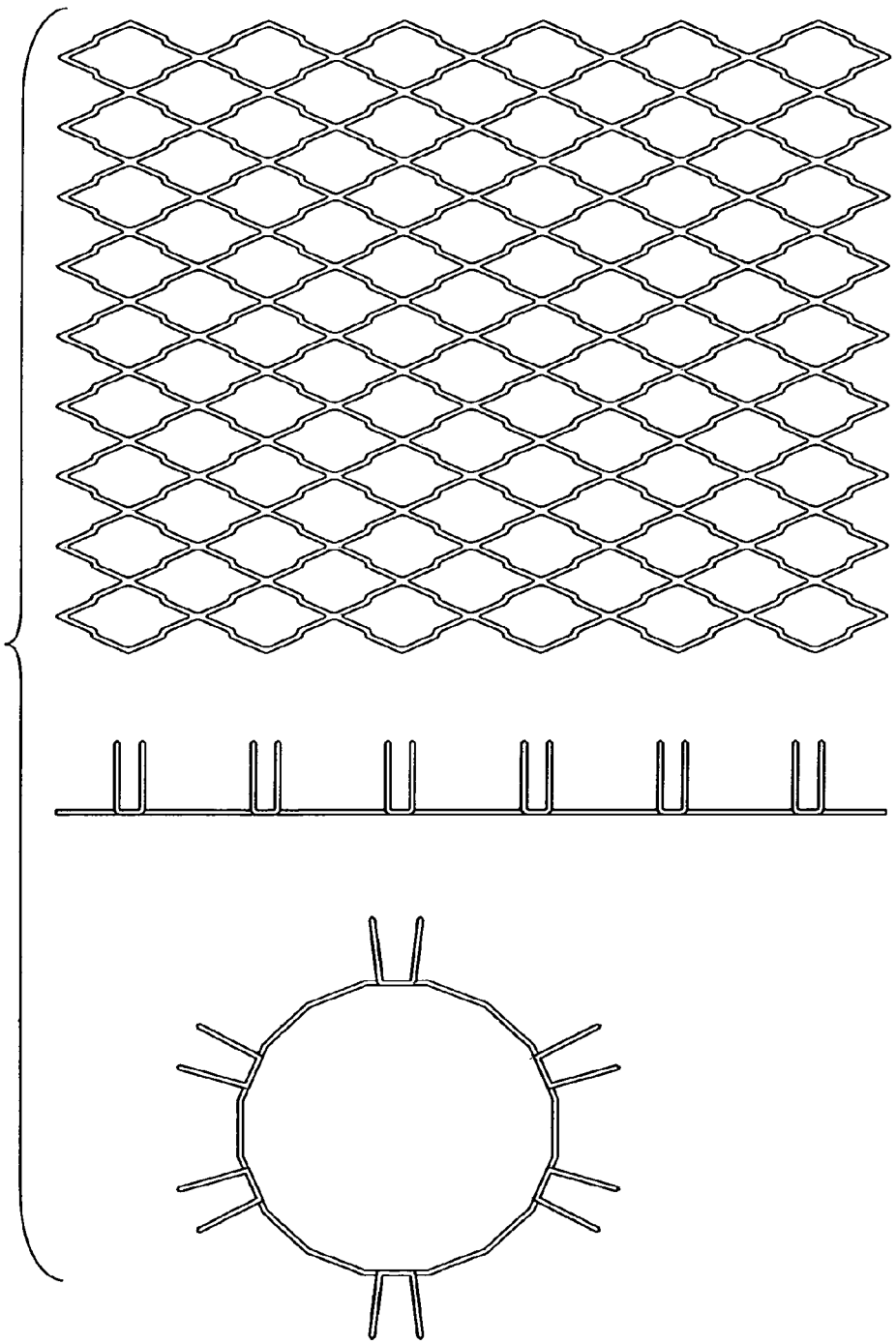

FIGS. 6A-6C show another embodiment for the delivery device in which the spikes (welded, bonded, or shaped out-of-plane) are married at joints on the circumference of an accordion-like structure provide for a mechanical expansion engagement with the plaque. In the pre-loaded delivery position shown in FIG. 6A, the accordion-like structure 60 is stretched longitudinally over the surface of the delivery catheter 61, and the spikes 62 lay flat against the catheter sheath. This position of the spike structure is used when the catheter is inserted and withdrawn. Once the spike structure is in position at the plaque site, the accordion-like structure 60 has its opposite ends moved together, such that the spikes 62 are pressed out radially to pierce the plaque, as shown in FIG. 6B. The compression of the accordion-like structure 60 may be actuated by mechanical pulley, polymer fiber or wire attached at points A disposed symmetrically around the circumference of the catheter. The wires are pulled uniformly at one end of the accordion-like structure to compress lattice segments of the structure and decrease the distance between the spike connector joints, thereby forcing the spikes outwardly toward the lumen wall. In FIG. 6C, the accordion-like structure is shown laid out in plan view and elevation view, and pre-loaded in end view.

Figure 7A:
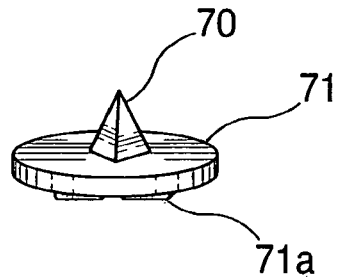
FIGS. 7A-7C show three variations for mounting a spike on a carrier.
Figure 7B:
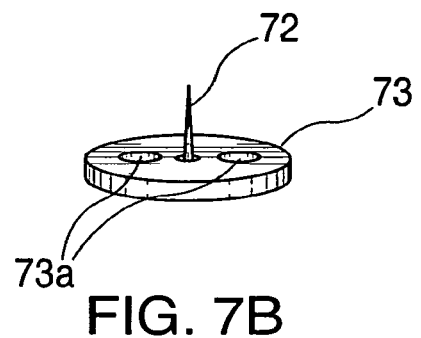
Figure 7C:
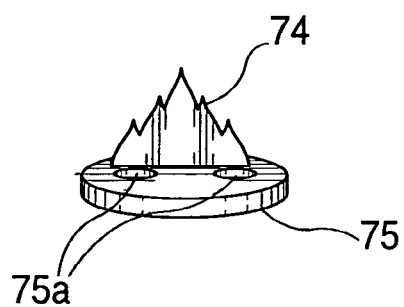

FIGS. 7A-7C show three variations for mounting a spike on a carrier. In FIG. 7A, the spike 70 (pyramid point) is mounted on a button 71 having lower shanks 71a for seating on a carrier. In FIG. 7B, the spike 72 (pin) is mounted on a button 73 having button holes 73a for attachment by fasteners to the carrier. In FIG. 7C, the spikes 74 (sharp tips) are mounted on a button 75 having holes 75a for fastening to the carrier. The buttons may be entwined within a fabric, woven pattern or bag structure using the button holes or mounting shanks on the buttons. These spike-mounting buttons may be used with any of the above-described embodiments for the delivery device.

Figure 8:
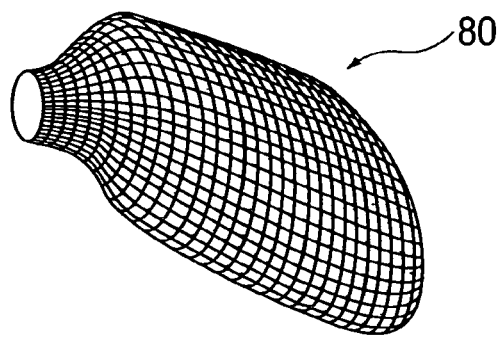
FIG. 8 illustrates an embodiment of the delivery device in which the spikes are carried on a stretchable mesh structure.
Figure 9A:
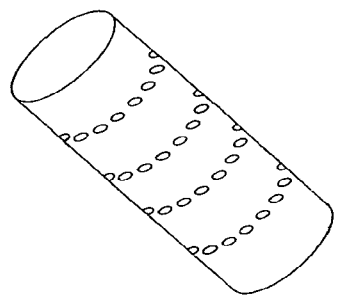
FIGS. 9A-9E illustrate various patterns for arrangement of the spikes on the delivery device.
Figure 9B:
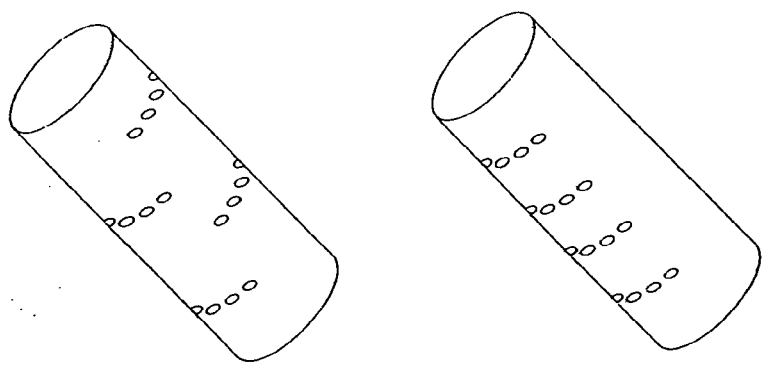
Figure 9C:
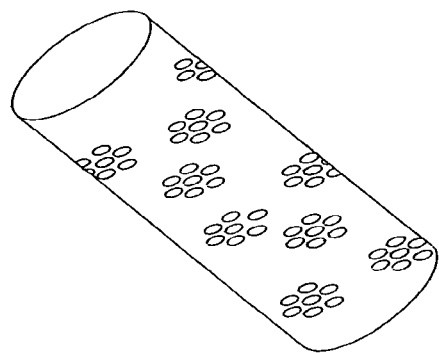
Figure 9D:
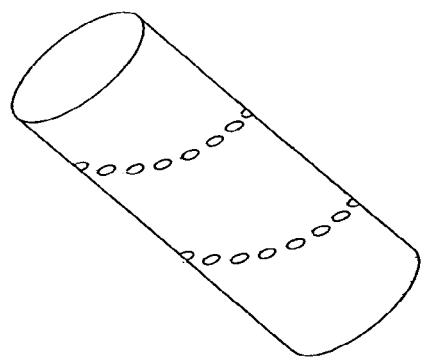
Figure 9E:
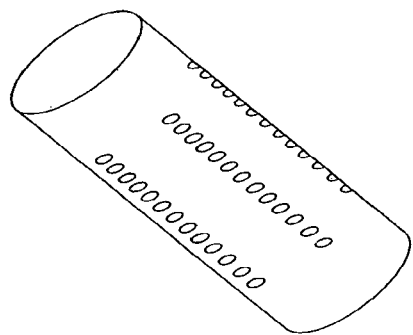

FIG. 8 shows an embodiment in which the spikes are carried on a stretchable mesh structure 80 surrounding an expansion balloon which is inflated to stretch the mesh outwardly on all sides and push the spikes into the surrounding plaque mass. The spikes may be interwoven into the mesh structure. When the balloon is deflated, the mesh snaps back with the collapsed surface of the expansion balloon.

In all the embodiments described above, the spikes may be made from metal, polymer, silicon or carbon composite (with or without an inert coating), a super-elastic material, or carbon nanotubes. The spikes may have a preferred height (from base to tip) of 0.05 mm to 1.0 mm. The spike tip may be needle-like with a needle head for mounting. As an alternative, the tip can be shaped with a thin tubular cross-section (as in a needle for transporting fluid through it), or a groove or slot having one dimension that is much larger than the other where the larger dimension of the groove is less than 2 mm and the smaller dimension is much less than the first, and a point where the overall head radius is small less than 0.4 mm (as in a pin head), or a collection of very small points where the overall head radius is less than 0.05 mm (as in carbon nanotubes). It may instead be formed by carbon nanotubes presenting a collection of very small points to form a sharp tip. The spikes may also be coated with, or provide transport for, plaque-inhibiting medication for deposition into the plaque site. In the preferred embodiments described above, the spikes may be mounted on the surface of a balloon, or on a catheter, or may be mounted on a mechanically actuated surface.

The spikes may have various shapes, may be made from a variety of materials, may be deployed in different ways, and may be attached to the delivery device using different methods. The spikes are arrayed in any desired pattern to create a cut-along-the-dotted-line serration in the plaque mass so that it can become a cleavage plane or expansion plane during dilatation by balloon angioplasty.

The configuration of the spikes may be oriented in different manners depending upon the arterial disease and the plaque formation requiring treatment. The spikes may also have through-holes or inner channels for eluting medication through the spike to the surface of the plaque.

FIGS. 9A-9E illustrate various patterns for arrangement of the spikes on the delivery device, i.e., circumferential, partial circumferential, patch, spiral/diagonal, and longitudinal. The configurations are designed for different functional purposes in managing atherosclerotic plaque or in ease of manufacture or ease of use. Plaque with certain characteristics, such as very heavy calcification, may be treated with spikes that are configured in more of a circumferential or diagonal pattern, crossing the line of blood flow, since this morphology of plaque tends to form clusters or mounds of calcium. The spikes that may not be able to perforate this type of plaque or portions of this type of plaque very readily, but may be able to cut around the areas of worse disease and permit the inner circumference of the whole artery to expand. The spikes are arranged generally longitudinally, consistent with the fracture characteristics of plaque in most situations and with most plaque morphologies, and may be configured in a straight line. The straight, longitudinal lines of spikes may be very short, consisting of five spikes or less and may be quite long, consisting of 100 spikes or more. The longitudinal lines of spikes may be very dose together, with as many as 20 lines distributed on the circumference of the artery luminal surface, or there may be as few as a single line of barbs or spikes. The lines of spikes may also be in a slight diagonal or in a zig-zag fashion. The configuration of the barbs or spikes is determined in accordance with the best expected mechanism for post-angioplasty plaque dissection. They are designed to create cleavage planes or expansion lines suitable for the expected composition of the plaque and the pressures expected to be exerted upon it. The orientation and depth of desired cleavage planes may vary significantly with the parameters for balloon angioplasty. The spikes may also be constructed so that they may provide delivery of medications. A cooperative structure such as a double-walled balloon for pressure infusion of a small amount of medication agent into the plaque wall or other functionality may also be included.

FIGS. 10A-10C show another embodiment for the spike carrier of the delivery device. In FIG. 10A, the spikes are carried on ribbon strips of a slitted metal sheet which has opposite ends that are joined by either welding into a tube or the strips are cut out of a tube leaving one end intact. The spikes may have various profiles, such as where the length of the spike base or head is equal to the width of the ribbon strip, or the spike base length is a fraction of the ribbon width and is centered at the middle of the ribbon strip, or where the spike base is a fraction of the ribbon width and positioned at varying locations across the ribbon width or may have multiple spikes at any given ribbon section of width. FIG. 10B is an elevation view of the sheet. FIG. 10C shows the sheet after heat treatment to provide a shape memory in which the ribbons are spring-biased radially outward toward the arterial wall for generating perforations in the plaque. The shape memory may be used alone for mechanical engagement of the spikes, or may be combined with an expansion balloon to allow greater control of forces to be applied.

FIGS. 11A-11C show a variation of the above-described embodiment in which the ribbons of the carrier sheet contain a series of holes. The holes serve as points for attachment of strings, cables, or wire elements, configured in such a way, that when pulled can provide additional "Support and force outward against the lumen wall. FIG. 11B is an elevation view of the sheet. FIG. 11C shows the sheet after heat treatment to provide a shape memory for spring-biasing the ribbons radially outward. The shape memory may be combined with an expansion balloon to allow greater control of forces to be applied.

FIGS. 12A-12C show another variation of the above-described embodiment in which both longitudinal ends of the tube are kept intact, leaving only the middle region with slitted ribbons. One end contains a series of holes which serve as points for attachment of strings or wire elements that when pulled can provide additional support and force outward against the lumen wall. FIG. 12B is an elevation view of the sheet. FIG. 12C shows the sheet after heat treatment to provide a shape memory for spring-biasing the middle section of ribbons radially outward.

A general procedure for the pre-angioplasty perforation and serration of a plaque site will now be described. A delivery catheter is constructed for the purpose of plaque perforation in an endovascular environment. A guidewire is threaded along an artery from a percutaneous access site or a surgical incision to a lesion intended for treatment. A catheter is passed over the guidewire with an end of its sheath maintained gas-tight and fluid-tight for operational control externally by an operator. Once the catheter is in position at the lesion site, a spike delivery device is advanced down the hollow, tubular shaft of the sheath over the guidewire. The delivery device for the typical perforation-serration catheter is intended to be as large as 8 Fr and more likely 5 Fr or less in diameter. The guidewire lumen may be 0.014 inches or up to 0.035 inches in diameter. The length of the delivery catheter may be as short as 40 cm but more likely 75 to 80 cm for a short length and 120 to 135 cm for a long length. The catheter has another tubular channel for inflating or actuating the expansion balloon or apparatus on the delivery end of the catheter.

When the expansion balloon, mechanical expansion apparatus or other apparatus is actuated, the spikes on the delivery device are pressed toward the plaque. The spikes are driven into the plaque and create multiple perforations forming intended serrations in the surface of the plaque in a proscribed pattern. The expansion balloon or apparatus is somewhat compliant and may be inflated further to compress the plaque and enlarge further. When the desired perforation of the plaque has been achieved, the expansion balloon or apparatus is de-actuated, disengaging the spikes from the plaque, and once collapsed is withdrawn through the catheter sheath.

After the preparation procedure for the plaque, the plaque can be compressed and the artery lumen safely and accurately dilated and stretched during standard balloon angioplasty to its intended diameter without creating numerous and substantial dissections and elevated flaps. The perforation and serration enable the plaque to be dilated more evenly and smoothly and avoid forming random cracks that may lead to dissection, arterial injury, and residual stenosis. The plaque, after it has been pre-treated with perforation and serration, may also be dilated with lower pressure (usually 2 atmospheres or less) than that which is used in standard balloon angioplasty. The lower intra-balloon pressure causes less injury to the artery wall. This "low pressure" or "minimal injury" angioplasty is less likely to cause the biological reaction that often follows balloon angioplasty with neointimal hyperplasia or smooth muscle cell replication.

In addition, the plaque is likely to expand with less fracturing or dissection during balloon angioplasty. This decreases the need for stent placement to be used to treat dissection or residual stenosis after balloon angioplasty. If extensive dissections and non-smooth luminal wall surfaces require a stent to be placed, the improved dilatation of the lumen obtained with pre-angioplasty perforation and serration would allow a stent to be more fully opened.

In cases where one or more local sites of post-angioplasty dissections or flaps present themselves, a thin, ring-shaped tack device may be placed at only the location of each specific problem site, so that the amount of foreign material emplaced as a retaining structure for plaque in the blood vessel can be minimized and exert only low lateral pressures against the post-angioplasty surface. A novel method and device for applying a ring-shaped tack device as a retaining structure for plaque in the blood vessel is described in U.S. patent application Ser. No. 11/955,331, filed Dec. 12, 2007, entitled "Device for Tacking Plaque to Blood Vessel Wall", which is incorporated by reference herein. The described procedure for perforation and serration of the plaque performed with a given amount of arterial dilatation may be sufficient to obtain compression of the plaque sufficiently that no balloon angioplasty or stent emplacement is required. Only one or a few of the ring-shaped tacks may be needed to secure the compressed plaque to the artery wall, thereby obtaining the desired medical treatment with minimal forces being applied to the arterial walls and with a minimum of foreign material emplaced in the body. The present invention is therefore deemed to include the alternative of combining the perforation and serration procedure with the procedure for applying localized tacks at specific locations for plaque retention.

It is to be understood that many modifications and variations may be devised given the above described principles of the invention. It is intended that all such modifications and variations be considered as within the spirit and scope of this invention, as defined in the following claims.

What is claimed is:

1. A method for treating atherosclerotic plaque intravascularly comprising:
   advancing a treatment device to a treatment site, the treatment device comprising:
      a tube having a longitudinal axis, the tube formed by a plurality of strips extending along the longitudinal axis, and a plurality of slits also extending along the longitudinal axis, each slit of the plurality of slits positioned between adjacent strips of the plurality of strips, the strips being connected at one or both ends; and
      a plurality of spikes on each of the plurality of strips, each spike extending a height from a base at the strip to a head, the base having a base width and a base length, the spike head having a length larger than the base width, the base length being larger than the base width, the spike head length and base length being perpendicular to the longitudinal axis;
   expanding the treatment device to force at least some of the spikes into contact with plaque at the treatment site;
   perforating the plaque at the treatment site to create a plurality of longitudinally extending rows of spaced apart linear incisions in the plaque with at least some of the spikes; and
   performing a balloon angioplasty to compress the plaque and enlarge the lumen at the treatment site, wherein performing a balloon angioplasty creates cleavage lines or planes in the plaque along the linear incisions in the plaque.

2. The method of claim 1, wherein perforating the plaque at the treatment site comprises creating a plurality of longitudinally extending rows of spaced apart parallel linear incisions in the plaque with at least some of the spikes.

3. The method of claim 1, wherein performing a balloon angioplasty comprises performing a balloon angioplasty at an expansion pressure of 4 atmospheres or less.

4. The method of claim 1, wherein performing a balloon angioplasty comprises performing a balloon angioplasty at an expansion pressure of 2 atmospheres or less.

5. The method of claim 1, wherein the steps of expanding and perforating further comprise actuating an expansion apparatus at an expansion pressure of 4 atmospheres or less.

6. The method of claim 1, further comprising transporting medication into the plaque with the spikes.

7. The method of claim 1, wherein expanding the treatment device comprises expanding a balloon positioned within the tube to force at least some of the spikes into contact with plaque at the treatment site.

8. The method of claim 1, wherein each spike of the plurality of spikes has a spike base equal to a width of the corresponding strip, such that the spike extends from a first slit on one side of the strip to a second slit on a second side of the strip, the first and second slits each being one of the plurality of slits.

9. The method of claim 1, wherein each strip of the plurality of strips comprises a single longitudinally extending strut, wherein expanding the treatment device comprises radially advancing at least a center portion of the strut to bow outwardly while continuing to extend longitudinally.

10. The method of claim 1, further comprising removing the treatment device from the treatment site before performing the balloon angioplasty.

11. The method of claim 1, wherein expanding the treatment device comprises inflating a first expansion balloon, the plurality of strips surrounding the first expansion balloon, and wherein performing the balloon angioplasty comprises inflating a second expansion balloon.

12. A method for treating atherosclerotic plaque intravascularly comprising:
   perforating and serrating atherosclerotic plaque as part of an angioplasty procedure comprising:
      expanding a treatment catheter at a treatment site, the treatment catheter having a longitudinal axis, a plurality of strips extending along the longitudinal axis and a row of linear spikes with elongated tips on each strip of the plurality of strips, the linear spikes and elongated tips each having a major axis and a minor axis, the major axis being perpendicular to the longitudinal axis of the treatment catheter;
      forming microperforations with at least some of the rows of linear spikes in a luminal surface of plaque at the treatment site, wherein the microperforations act as linear serrations for forming cleavage lines or planes in the plaque during an angioplasty procedure; and
      withdrawing the linear spikes from the treatment site.

13. The method of claim 12, further comprising performing a balloon angioplasty to compress the plaque and enlarge the lumen at the treatment site.

14. The method of claim 13, wherein performing a balloon angioplasty comprises performing a balloon angioplasty at an expansion pressure of 4 atmospheres or less.

15. The method of claim 13, wherein expanding the treatment catheter comprises inflating a first expansion balloon, the plurality of strips surrounding the first expansion balloon, and wherein performing the balloon angioplasty comprises inflating a second expansion balloon.

16. The method of claim 12, wherein the steps of expanding and forming further comprise actuating an expansion apparatus at an expansion pressure of 4 atmospheres or less.

17. The method of claim 12, further comprising transporting medication into the plaque with the spikes.

18. The method of claim 12, wherein expanding the treatment catheter comprises expanding a balloon positioned within the plurality of strips to force at least some of the spikes into contact with plaque at the treatment site.

19. The method of claim 12, wherein each spike of the plurality of spikes has a spike base equal to a width of the corresponding strip, such that the spike extends from a first slit on one side of the strip to a second slit on a second side of the strip, the first and second slits each being one of the plurality of slits.

20. The method of claim 12, wherein each strip of the plurality of strips comprises a single longitudinally extending strut, wherein expanding the treatment device comprises radially advancing at least a center portion of the strut to bow outwardly while continuing to extend longitudinally.

* * * * *